(12) United States Patent
Angelopoulos et al.

(10) Patent No.: US 9,918,831 B2
(45) Date of Patent: Mar. 20, 2018

(54) ASPHERIC OPTICAL LENSES AND ASSOCIATED SYSTEMS AND METHODS

(75) Inventors: Robert Angelopoulos, Fort Worth, TX (US); Stephen J. Van Noy, Southlake, TX (US)

(73) Assignee: Novartis AG, Lichtstrasse, Basel (CH)

( * ) Notice: Subject to any disclaimer, the term of this patent is extended or adjusted under 35 U.S.C. 154(b) by 712 days.

(21) Appl. No.: 13/316,692

(22) Filed: Dec. 12, 2011

(65) Prior Publication Data

US 2012/0158131 A1    Jun. 21, 2012

Related U.S. Application Data

(60) Provisional application No. 61/423,475, filed on Dec. 15, 2010.

(51) Int. Cl.
| | | |
|---|---|---|
| *A61F 2/16* | (2006.01) | |
| *B29D 11/02* | (2006.01) | |
| *G02C 7/04* | (2006.01) | |

(52) U.S. Cl.
CPC ............ *A61F 2/1616* (2013.01); *A61F 2/164* (2015.04); *B29D 11/023* (2013.01); *G02C 7/042* (2013.01)

(58) Field of Classification Search
CPC .............................. A61F 2/164; A61F 2/1616
USPC .............................. 623/6.23, 6.24, 6.27–6.29
See application file for complete search history.

(56) References Cited

U.S. PATENT DOCUMENTS

| | | | |
|---|---|---|---|
| 6,540,353 B1* | 4/2003 | Dunn | 351/159.47 |
| 7,018,409 B2 | 3/2006 | Glick et al. | |
| 7,073,906 B1 | 7/2006 | Portney | |
| 2004/0156014 A1* | 8/2004 | Piers et al. | 351/168 |
| 2004/0230299 A1* | 11/2004 | Simpson | A61F 2/1613 |
| | | | 623/6.11 |
| 2006/0116764 A1 | 6/2006 | Simpson | |
| 2006/0212117 A1* | 9/2006 | Lang et al. | 623/6.23 |
| 2009/0059163 A1 | 3/2009 | Pinto | |
| 2009/0164008 A1 | 6/2009 | Hong et al. | |
| 2010/0228345 A1 | 9/2010 | Bille | |
| 2010/0315589 A1* | 12/2010 | Portney | 351/160 R |

FOREIGN PATENT DOCUMENTS

| | | |
|---|---|---|
| EP | 0480748 A1 | 4/1992 |
| EP | 0741314 A2 | 6/1996 |
| JP | 2007510521 A | 4/2007 |

(Continued)

*Primary Examiner* — Corrine McDermott
*Assistant Examiner* — Joshua Levine (57) ABSTRACT

Aspheric optical lenses (e.g., intraocular lenses and contact lenses) are provided. The intraocular lens includes a body portion defining an anterior optical surface and an opposing posterior optical surface. The anterior optical surface includes a central region surrounded by a first outer region and a second outer region. The central region has a first asphericity profile. The first outer region has a second asphericity profile that is different than the first asphericity profile of the central region. The second outer region has a third asphericity profile that is different than the second asphericity profile of the first outer region. The overall asphericity profile of the optical lens provides different depths of focus for different pupil sizes. The result is an optical lens that provides increased depth of focus or pseudo-accommodation while maintaining desired optical power and performance.

10 Claims, 9 Drawing Sheets

(56) References Cited

FOREIGN PATENT DOCUMENTS

| WO | 97/12272 A1 | 4/1997 |
| WO | 2005/046527 A2 | 5/2005 |
| WO | 2005/077300 A2 | 8/2005 |
| WO | 2010009254 A1 | 1/2010 |

* cited by examiner

ASPHERIC OPTICAL LENSES AND ASSOCIATED SYSTEMS AND METHODS

RELATED APPLICATIONS

This application claims priority under 35 USC § 119 to U.S. provisional application Ser. No. 61/423,475, filed on Dec. 15, 2010.

BACKGROUND OF THE INVENTION

This invention relates generally to the field of optical lenses and, more particularly, to the optical design of intraocular lenses (IOLs) and contact lenses.

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial IOL.

The majority of cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial IOL. The optical power of the natural crystalline lens can vary under the influence of the ciliary muscles to provide accommodation for viewing objects at different distances from the eye. Many IOLs, however, provide a monofocal power with no provision for accommodation. Further, some IOLs compensate for corneal aberrations by including aspheric surfaces that are designed to counteract the asphericity of the patient's cornea by greatly reducing, or eliminating all together, the overall aberrations of the eye. While IOLs fabricated based on these techniques may increase image contrast, they generally result in a decrease in the patient's depth of field.

Therefore, there remains a need for improved IOLs that can provide pseudo-accommodative optical power with increased depth of field so that sharp optical images are provided over a wide range of pupil sizes.

SUMMARY OF THE INVENTION

The present disclosure provides optical lens designs for use with IOLs and contact lenses.

In one embodiment, an intraocular lens is provided. The intraocular lens includes a body portion defining an anterior optical surface and an opposing posterior optical surface. The intraocular lens is a monofocal lens in some instances. The anterior optical surface includes a central region surrounded by a first outer region and a second outer region. The central region extends radially outward from a center point of the body portion and has a first asphericity profile. The first outer region extends radially outward from the central region and has a second asphericity profile that is different than the first asphericity profile of the central region. Finally, the second outer region extends radially outward from the first outer region and has a third asphericity profile that is different than the second asphericity profile of the first outer region. In some instances, each of the central region, the first outer region, and the second outer region have the same base power and/or conic constant.

In some embodiments, the first outer region comprises an annular ring surrounding the central region such that the first outer region has a circular inner boundary defined by a first distance from the center point (equal to the radius of the outer boundary of the central region) and a circular outer boundary defined by a second distance from the center point. Similarly, the second outer region may comprise an annular ring surrounding the first outer region such that the second outer region has a circular inner boundary defined by the second distance and a circular outer boundary defined by a third distance from the center point. In some instances of such embodiments, the first distance is between about 1.0 mm and about 2.0 mm, the second distance is between about 1.5 mm and about 2.5 mm, and the third distance is between about 2.5 mm and about 3.5 mm. In that regard, in some embodiments the circular outer boundary of the second outer region is an outer boundary of the intraocular lens. In other embodiments, the lens includes one or more additional outer regions extending radially outward from the second outer region. In such embodiments, the one or more additional outer regions have an asphericity profile that is different from at least the adjacent regions.

In some embodiments, each of the first asphericity profile, the second asphericity profile, and the third asphericity profile are defined by the same equation. In one embodiment, the asphericity profiles are defined by the following equation:

$$Sag = \frac{cr^2}{1 + \sqrt{1-(1+k)c^2r^2}} + \alpha_2 r^4 + \alpha_3 r^6,$$

where c, k, $\alpha_2$, and $\alpha_3$ are constants and r is a radius from the center point. In some instances, constants c and k have the same value for each of the first, second, and third asphericity profiles. In some instances, each of $\alpha_2$ and $\alpha_3$ has a different value for each of the first, second, and third asphericity profiles. The overall asphericity profile of the intraocular lens defined by the regions provides different depths of focus for different pupil sizes. The result is an intraocular lens that provides increased depth of focus or pseudo-accommodation while maintaining desired optical power and performance.

In another embodiment, a method of manufacturing an optical lens is provided. The method includes shaping a central region, a first outer region, and a second outer region of an anterior surface of an optical lens. In that regard, the central region extends radially outward from a center point of the lens a first distance such that the central region has a circular outer boundary, while the first outer region extends radially outward from the central region such that an inner boundary of the first outer region is defined by the circular outer boundary of the central region and an outer boundary of the first outer region is defined by a second distance greater than the first distance such that the first outer region is concentric with the central region. Similarly, the second outer region extends radially outward from the first outer region such that an inner boundary of the second outer region is defined by the outer boundary of the first outer region and an outer boundary of the second outer region is defined by a third distance greater than the second distance such that the second outer region is concentric with the first outer region and the central region.

The central region is shaped to have a first asphericity profile; the first outer region is shaped to have a second asphericity profile different than the first asphericity profile; and the second outer region of the anterior surface to have a third asphericity profile different than the second asphericity profile. The different asphericity profiles provide different depths of focus for different pupil sizes. The resulting optical lens provides an overall increased depth of focus or pseudo-accommodation while maintaining desired optical power and performance. In some instances, each of the central region, the first outer region, and the second outer region are shaped such that the central region, the first outer region, and the second outer region have the same base power and the same conic constant. In some embodiments, the method also includes shaping a posterior surface of the optical lens to have a spherical profile. In other embodiments, the method includes shaping a posterior surface of the optical lens to have a toric profile.

In another embodiment, an optical lens is provided. The optical lens includes a body portion defining an anterior optical surface and an opposing posterior optical surface. The anterior optical surface includes a central region extending radially outward from a center point of the lens a first distance such that the central region has a circular outer boundary, an annular ring extending radially outward from and concentric with the central region, and an outer region extending radially outward from and concentric with the annular ring. The central region has a first asphericity profile, the annular ring has a second asphericity profile different than the first asphericity profile, and the outer region has a third asphericity profile different than the second asphericity profile. In some instances, the central region, the annular ring, and the outer region have equivalent base powers and conic constants. In some embodiments, the posterior optical surface has a profile selected from the group consisting of a spherical profile and a toric profile.

The present disclosure provides optical lens designs that vary the amount of asphericity through different regions of an optical surface to provide different depths of focus for different pupil sizes. The varying asphericity profiles in the different regions results in an optical lens that provides quality distance vision while providing an increase of depth of focus for improved near vision. In that regard, the asphericity profiles can be varied to provide up to three diopters of increased depth of focus or pseudo-accommodation in a stationary optic.

Other aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure.

As an initial matter, the following description will discuss aspects of the present disclosure in the context of an intraocular lens. However, this is for sake of clarity and conciseness and does not in any way limit application of the present disclosure to any particular type of lens. Rather, it is understood that the aspects of the present disclosure discussed below in the context of intraocular lenses are equally applicable to other optical lenses utilized for improving patient vision. In that regard, the aspheric optical design aspects described herein with respect to intraocular lenses are similarly incorporated into contact lenses in some instances. Accordingly, the aspheric optical designs of the present disclosure are understood to have broad application to various types of lenses as would be understood by one skilled in the art.

Figure 1:
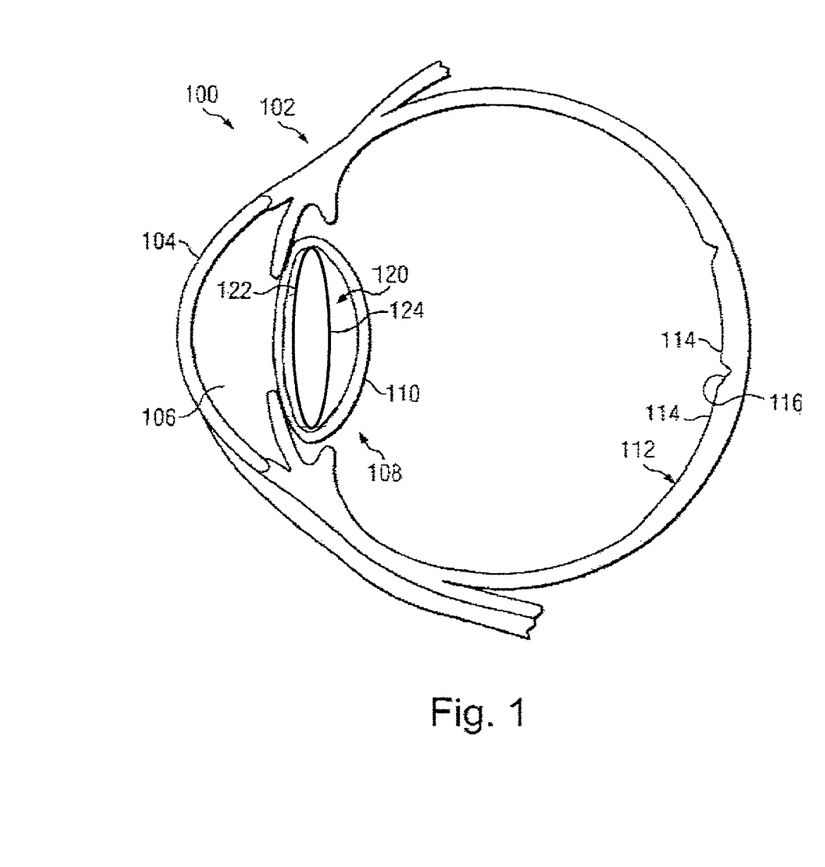
FIG. 1 is a diagrammatic cross-sectional side view of an eye with an implanted intraocular lens according to one aspect of the present disclosure.

Referring to FIG. 1, shown therein is an arrangement 100 illustrating aspects of the present disclosure. In that regard, FIG. 1 is a diagrammatic cross-sectional side view of an eye 102. The eye 102 includes a cornea 104, an anterior chamber 106, and a posterior chamber 108. A capsular bag 110 is illustrated in the posterior chamber 108. The eye 102 further includes a retina 112, including macula 114 and fovea 116. An intraocular lens 120 is implanted in the posterior chamber 108. In particular, the intraocular lens 120 is implanted within the capsular bag 110. The intraocular lens 120 includes an anterior optical surface 122 and a posterior optical surface 124. The anterior and posterior optical surfaces 122 and 124 define a monofocal lens. Accordingly, with intraocular lens 120 energy is not split between two foci. As will be discussed in greater detail below, in some embodiments the anterior optical surface 122 is aspheric, while the posterior optical surface 124 is spherical or toric.

Figure 2:
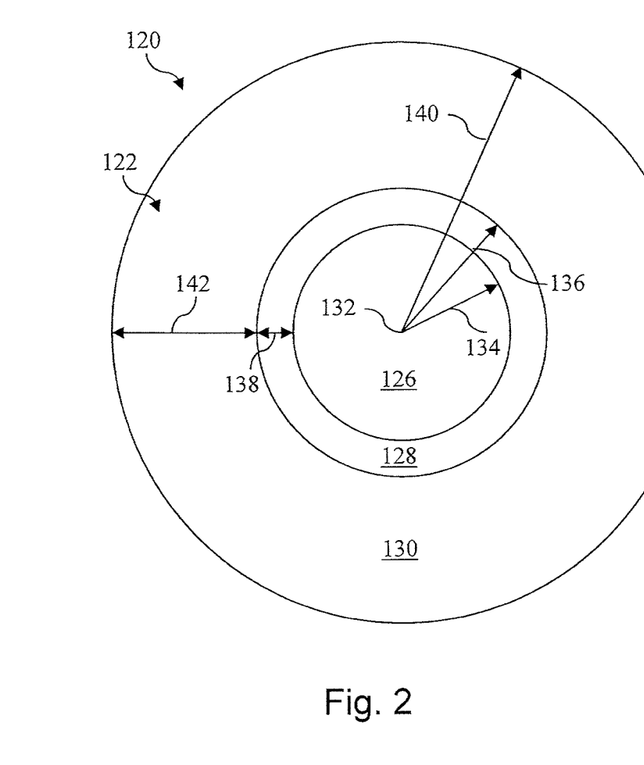
FIG. 2 is a front view of the intraocular lens of FIG. 1.

Referring now to FIG. 2, shown therein is a front view of the intraocular lens 120. In particular, the anterior optical surface 122 of the intraocular lens 120 is shown. In that regard, the anterior optical surface 122 includes three regions 126, 128, and 130 extending about a center point 132. As shown, each of the regions 126, 128, and 130 has a generally circular profile when viewed from the front. Region 126 is defined by a radius 134 extend from the center point 132. Generally, radius 134 is between about 0.01 mm and about 1.8 mm and, in some instances, is between about 0.25 mm and about 1.5 mm. Region 128 extends radially outward from region 126. Accordingly, the inner boundary of the region 128 is defined by radius 134 while the outer boundary of region 128 is defined by radius 136. Generally, radius 136 is between about 0.02 mm and about 2.5 mm and, in some instances, is between about 0.5 mm and about 2.0 mm. Accordingly, region 128 has a radial thickness 138 extending between its inner boundary and its outer boundary. Generally, radial thickness 138 is between about 0.01 mm and about 1.75 mm. Finally, region 130 extends radially outward from region 138. Accordingly, the inner boundary of the region 130 is defined by radius 136 while the outer boundary of region 130 is defined by radius 140. Radius 140 defines the optic semi-diameter and generally ranges from about 12.5 mm to about 3.0 mm. Accordingly, region 130 has a radial thickness 142 extending between its inner boundary and its outer boundary. Generally, radial thickness 142 is between about 0.01 mm and about 3.0 mm.

As will be discussed in greater detail below, region 126 has a first asphericity profile, region 128 has a second asphericity profile that is different than the asphericity profile of region 126, and region 130 has a third asphericity profile that is different than the asphericity profile of the region 128. In some instances, the asphericity profile of region 130 is also different than the asphericity profile of the region 126 such that each region of the anterior optical surface 122 has a different asphericity profile. However, the regions 126, 128, and 130 have the same base power and conic constant. The overall asphericity profile of the anterior optical surface 122 defined by the regions 126, 128, and 130 provides different depths of focus for different pupil sizes. The result is that the intraocular lens 120 provides an increased depth of focus or pseudo-accommodation while maintaining the desired optical power and performance.

The asphericity profiles of each of the regions 126, 128, and 130 are defined by the same equation, specifically $$Sag = \frac{cr^2}{1+\sqrt{1-(1+k)c^2r^2}} + \alpha_2 r^4 + \alpha_3 r^6 \qquad \text{(Equation 1)}$$

where c, k, $\alpha_2$, and $\alpha_3$ are constants and r is a radius from the center point 132 of the anterior optical surface 122. In some embodiments, c has the same value for calculating the asphericity profiles for each of the regions 126, 128, and 130. Similarly, in some embodiments k has the same value for calculating the asphericity profiles for each of the regions 126, 128, and 130. Accordingly, in some instances both c and k maintain the same value across each of regions 126, 128, and 130 for calculating the asphericity profiles. On the other hand, in some embodiments $\alpha_2$ has a different value for calculating the asphericity profiles for each of the regions 126, 128, and 130. Also, in some instances $\alpha_3$ has a different value for calculating the asphericity profiles for each of the regions 126, 128, and 130. Accordingly, in some instances both $\alpha_2$ and $\alpha_3$ have varying values across the regions 126, 128, and 130 for calculating the asphericity profiles. Thus, in some particular instances c and k maintain the same value across each of regions 126, 128, and 130, while the values of $\alpha_2$ and $\alpha_3$ vary across the regions 126, 128, and 130 for calculating the asphericity profiles.

Figure 3:
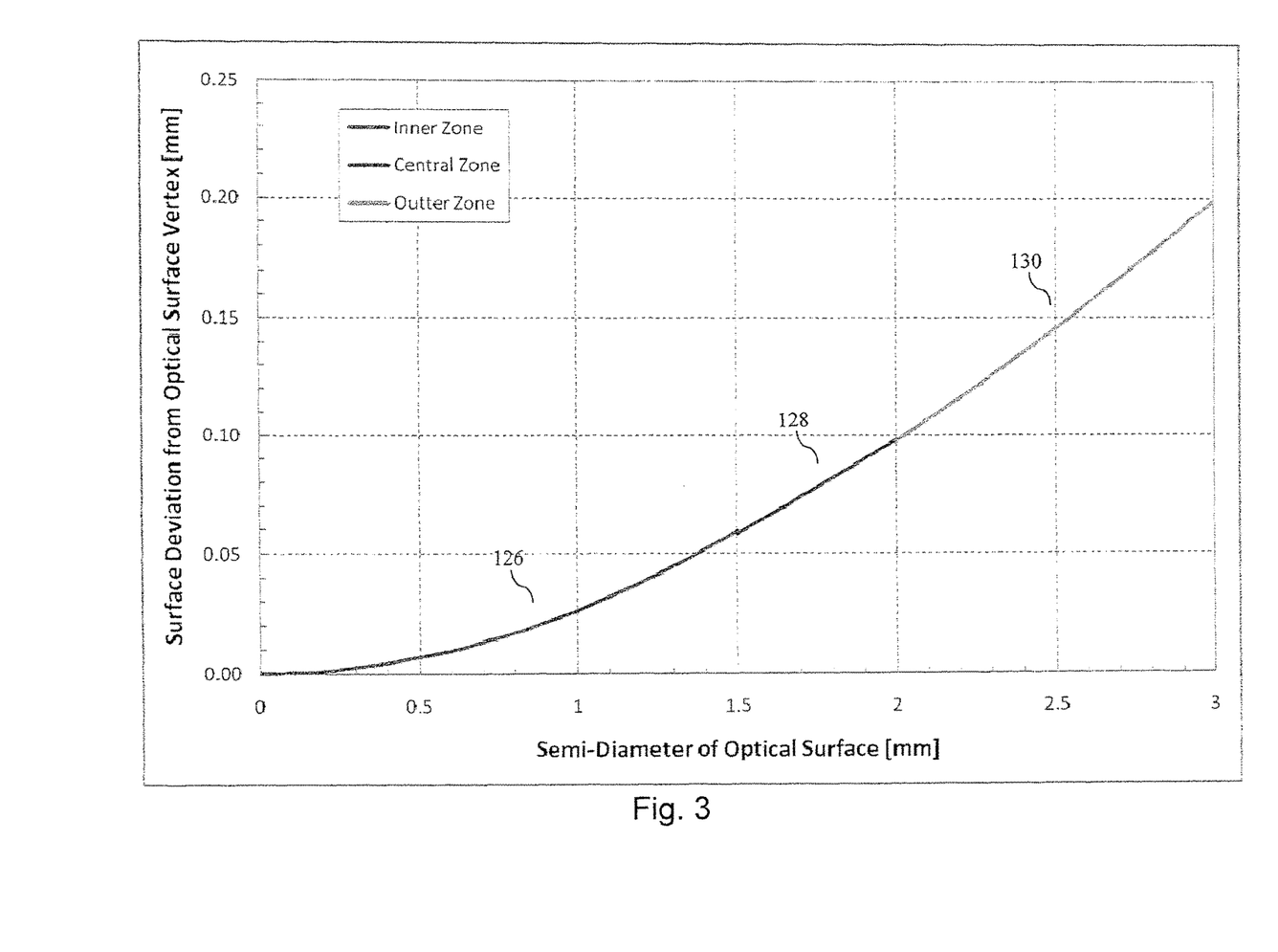
FIG. 3 is a graph illustrating an anterior surface profile of the intraocular lens of FIGS. 1 and 2 according to an exemplary embodiment of the present disclosure.

Referring now to FIG. 3, shown therein is a graph illustrating the asphericity surface profile of anterior optical surface 122 according to an exemplary embodiment of the present disclosure. In particular, the graph of FIG. 3 maps the surface deviation from the optical surface vertex (in mm) as compared to the semi-diameter or radius of the optical surface (in mm). As shown, the graph illustrates the asphericity profiles for each of the regions 126, 128, and 130. In the illustrated embodiment the asphericity profiles for each of the regions 126, 128, and 130 is calculated using Equation 1 above. In that regard, for region 126, where r has values between 0.0 mm and 1.5 mm, the following constant values are used: 1/c=18.990, k=−3.159, $\alpha_2$=6.034E-05, and $\alpha_3$=1.164E-05. For region 128, where r has values between 1.5 mm and 2.0 mm, the following constant values are used: 1/c=18.990, k=−3.159, $\alpha_2$=1.930E-04, and $\alpha_3$=−1.527E-04. Finally, for region 130, where r has values between 2.0 mm and 3.0 mm, the following constant values are used: 1/c=18.990, k=−3.159, $\alpha_2$=−4.680E-04, and $\alpha_3$=3.541E-06.

In some instances, the specific values for the $\alpha_2$ and $\alpha_3$ coefficients are selected based on targets established within a merit function. In that regard, in some embodiments the targets specify the magnitude of the desired depth of focus. Based on the desired targets the merit function will vary the $\alpha_2$ and $\alpha_3$ coefficients until they are optimized such that the merit function is minimized. Such optimization provides a design that best matches the targeted performance parameters input into the merit function.

Figure 4:
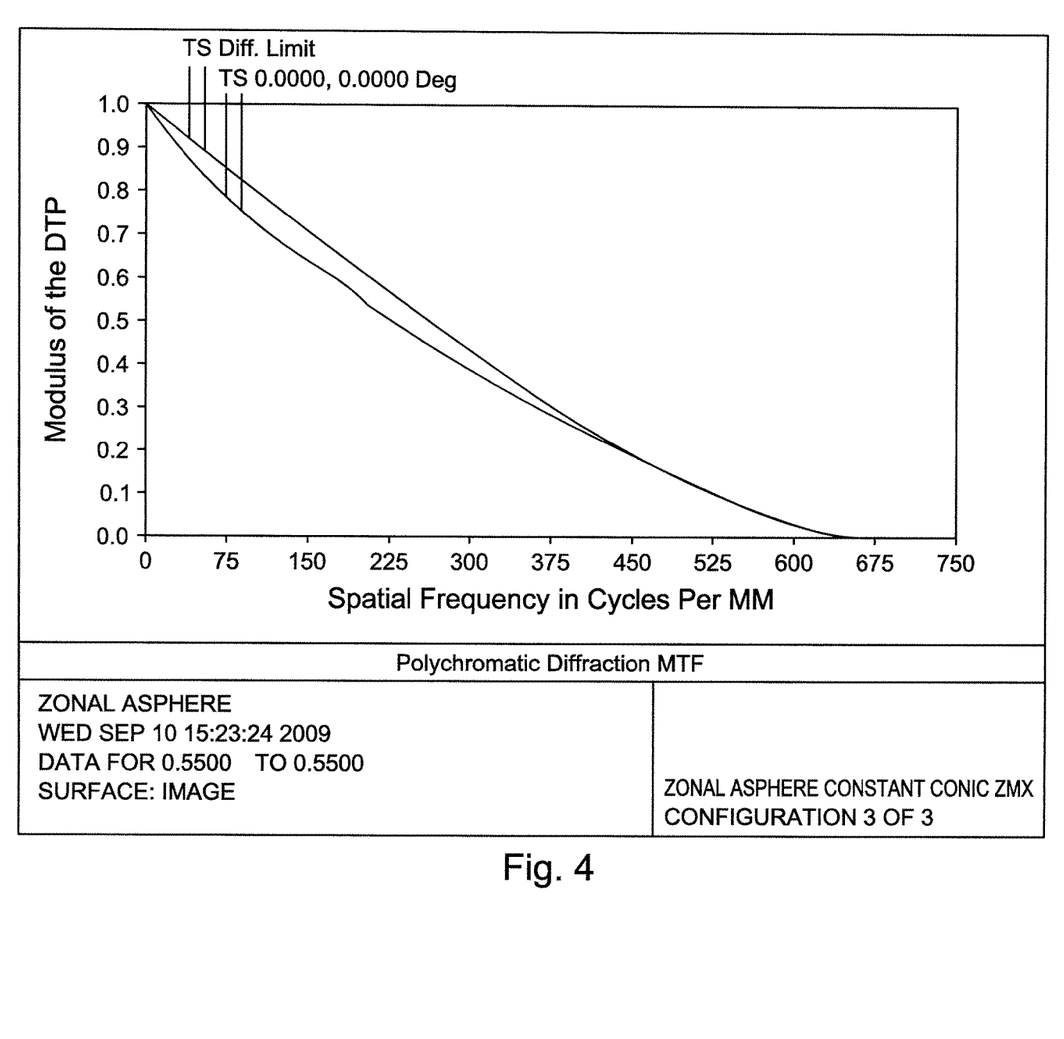
FIG. 4 is an MTF plot for the intraocular lens of FIGS. 1-3 with respect to an entrance pupil diameter (EPD) of 6.0 mm.
Figure 5:
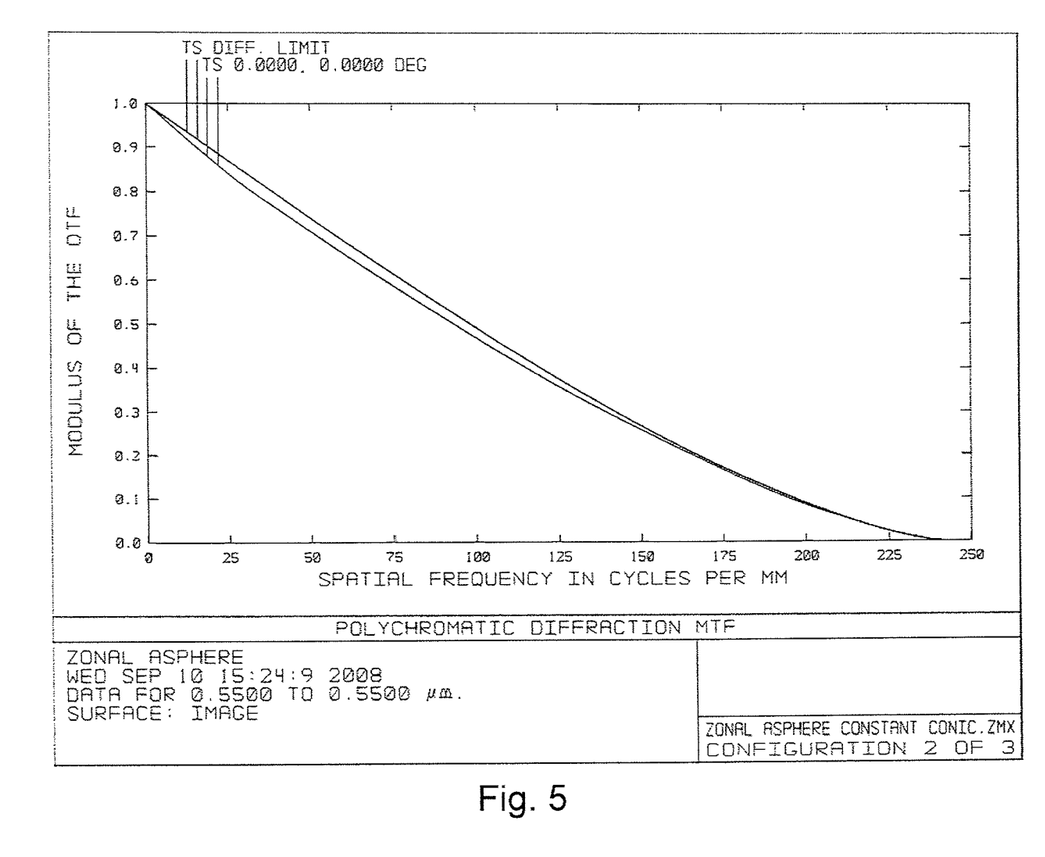
FIG. 5 is an MTF plot for the intraocular lens of FIGS. 1-3 similar to that of FIG. 4, but illustrating an MTF plot with respect to an entrance pupil diameter (EPD) of 2.0 mm.
Figure 6:
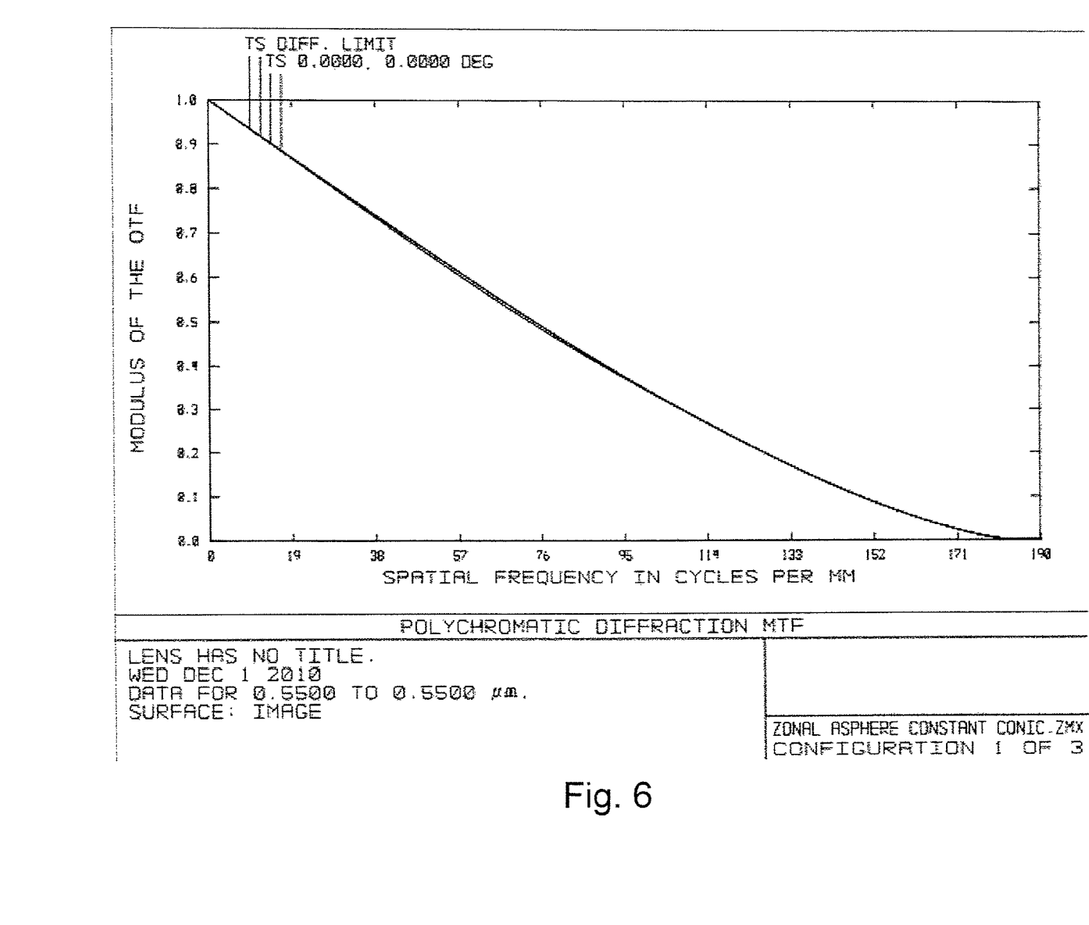
FIG. 6 is an MTF plot for the intraocular lens of FIGS. 1-3 similar to that of FIGS. 4 and 5, but illustrating an MTF plot with respect to an entrance pupil diameter (EPD) of 1.5 mm.

Referring now to FIGS. 4-6, shown therein are modulation transfer function (MTF) plots for the intraocular lens 120 at various entrance pupil diameters. In particular, the MTF plots map the modulus of the optical transfer function (OTF) relative to a spatial frequency (in cycles per mm). Further, each MTF plot maps the actual calculations relative to the intraocular lens 120 to corresponding theoretical limits of such a lens. FIG. 4 is an MTF plot for the intraocular lens 120 with respect to an entrance pupil diameter (EPD) of 6.0 mm. FIG. 5 is an MTF plot for the intraocular lens 120 with respect to an entrance pupil diameter (EPD) of 2.0 mm. Finally, FIG. 6 is an MTF plot for the intraocular lens 120 with respect to an entrance pupil diameter (EPD) of 1.5 mm. These MTF plots are calculated with the inclusion of all three regions 126, 128, and 130 of the intraocular lens 120. As shown in the MTF plots of FIGS. 4-6, the aspheric profiles of regions 126, 128, and 130 have minimal impact on the overall optical performance of the intraocular lens. In that regard, the intraocular lens 120 provides quality distance vision and, as discussed below with respect to FIGS. 7 and 8, also provides an increased depth of focus for improved near vision.

Figure 7:
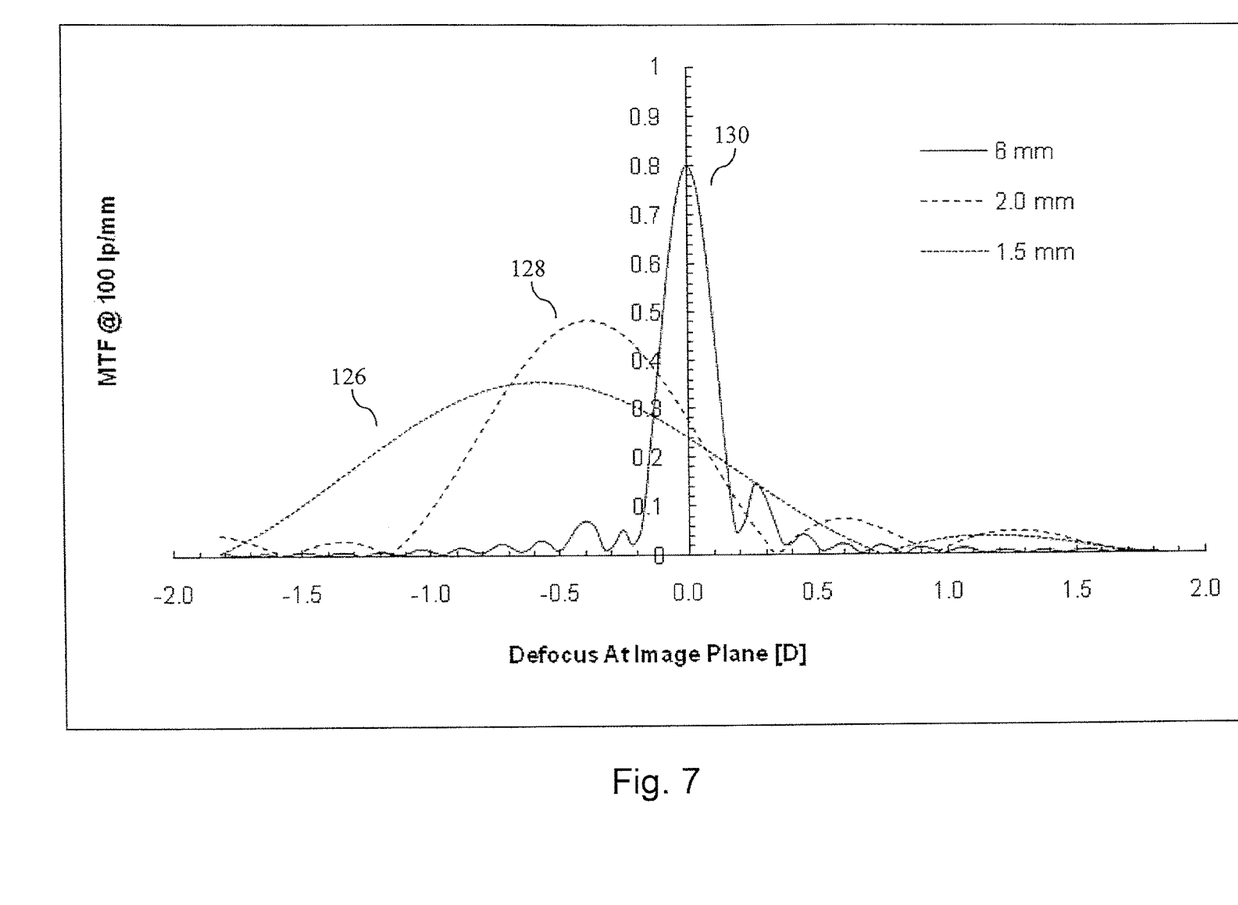
FIG. 7 is graph illustrating the through focus MTF for the intraocular lens of FIGS. 1-3 at 100 lp/mm (equivalent to 20/20 vision).
Figure 8:
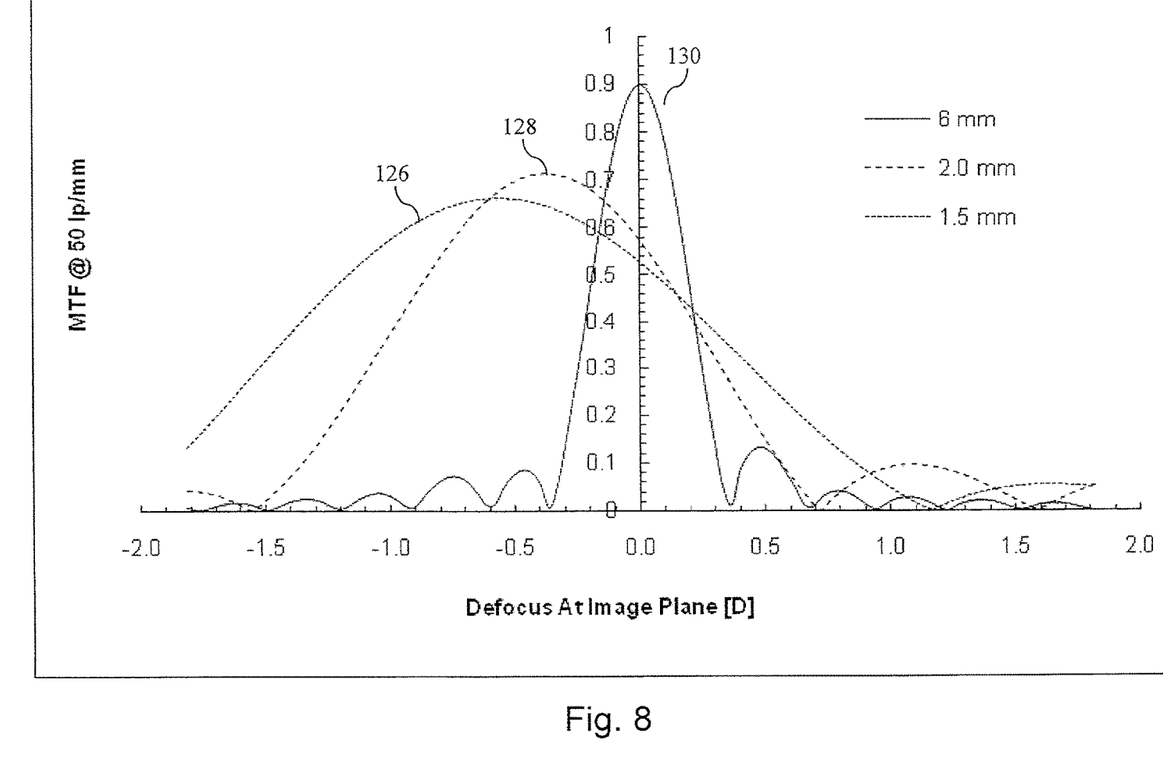
FIG. 8 is graph illustrating the through focus MTF for the intraocular lens of FIGS. 1-3 similar to that of FIG. 7, but at 50 lp/mm (equivalent to 20/40 vision).

Referring now to FIGS. 7 and 8, shown therein are graphs illustrating the through focus MTF for intraocular lens 120 at different line pairs per millimeter (lp/mm) for the each of the regions 126, 128, and 130. In particular, FIG. 7 is graph illustrating the through focus MTF for the intraocular lens 120 at 100 lp/mm, which is equivalent to 20/20 vision, for region 130 (6.0 mm), region 128 (2.0 mm), and region 126 (1.5 mm). FIG. 8 is graph illustrating the through focus MTF for the intraocular lens 120 at 50 lp/mm, which is equivalent to 20/40 vision, for region 130 (6.0 mm), region 128 (2.0 mm), and region 126 (1.5 mm).

Referring more specifically to FIG. 7, as shown, for region 130 at 20/20 vision there is no myopic shift and a very high MTF, which results in narrow through focus that provides quality distance vision at large pupil sizes. For region 128 at 20/20 vision, there is a myopic shift that introduces approximately 0.4 diopters of increased power with a broadened through focus. Finally, for region 126 at 20/20 vision, there is a myopic shift that introduces approximately 0.6 diopters of increased power with a further broadened through focus as compared to even region 128. As shown, even with the increased power provided by the optical profiles of regions 126 and 128, those regions maintain a relatively high MTF for quality distance vision. Accordingly, at the equivalent of 20/20 vision the intraocular lens 120 provides an increased depth of focus for improved near vision while maintaining the desired improvement in distance vision. In some instances, the asphericity profiles of region 126 and/or region 128 provide up to three diopters of increased depth of focus.

Referring now to FIG. 8, as shown, for region 130 at 20/40 vision there is no myopic shift and a very high MTF, which results in narrow through focus that provides quality distance vision at large pupil sizes. For region 128 at 20/40 vision, there is a myopic shift that introduces approximately 0.35 diopters of increased power with a broadened through focus. Finally, for region 126 at 20/40 vision, there is a myopic shift that introduces approximately 0.55 diopters of increased power with a further broadened through focus as compared to even region 128. As shown, even with the increased power provided by the optical profiles of regions 126 and 128, those regions maintain a relatively high MTF for quality distance vision. Accordingly, at the equivalent of 20/40 vision the intraocular lens 120 provides an increased depth of focus for improved near vision while maintaining the desired improvement in distance vision. In some instances, the asphericity profiles of region 126 and/or region 128 provide up to three diopters of increased depth of focus.

Figure 9:
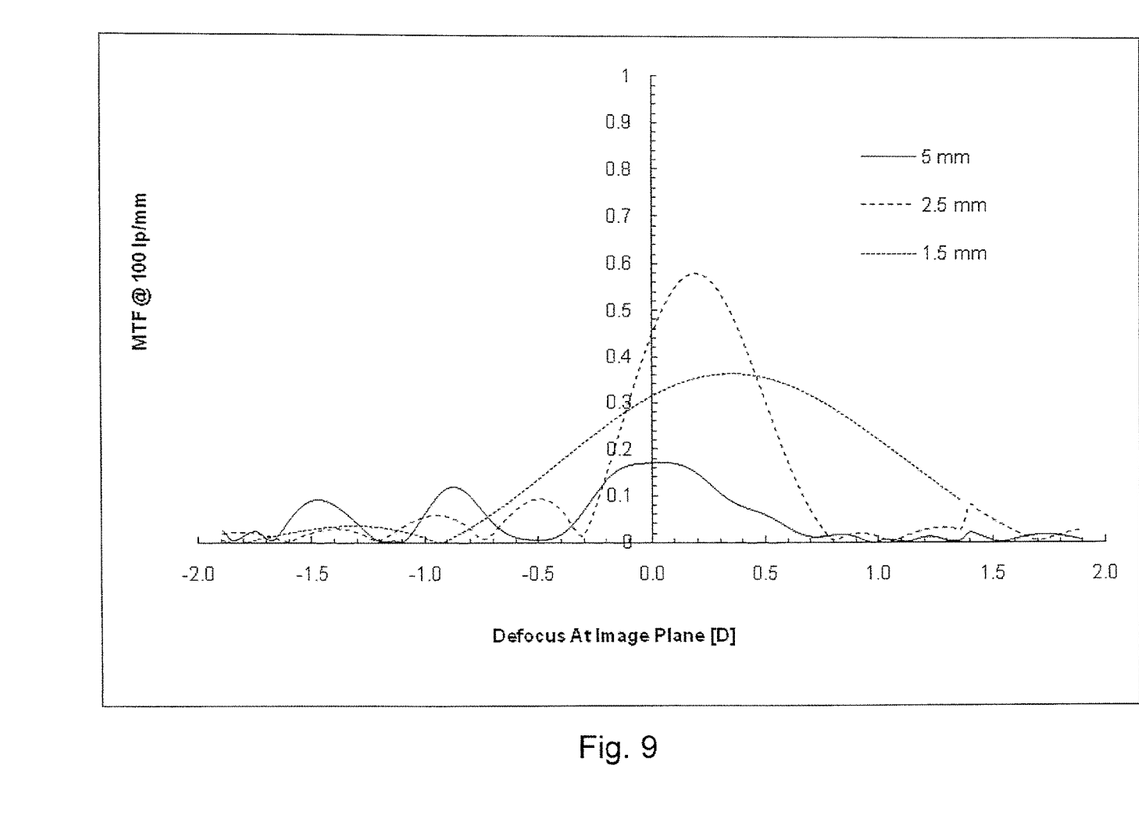
FIG. 9 is graph illustrating the through focus MTF for an intraocular lens at 100 lp/mm (equivalent to 20/20 vision), similar to that of FIG. 7, but for an intraocular lens with a standard spherical optical surface.

Referring now to FIG. 9, shown therein is a graph illustrating the through focus MTF for an intraocular lens with a standard spherical surface instead of the aspherical designs of the present disclosure. In particular, FIG. 9 is graph illustrating the through focus MTF for such a spherical intraocular lens at 100 lp/mm, which is equivalent to 20/20 vision. As shown, when the best focus of the lens is set for larger pupil diameters (e.g., 5 mm) and the pupil size is reduced, then focus shifts to the hyperopic side. This is a result of the positive spherical aberration in a standard spherical lens. In contrast, the asphericity profiles of the different regions of the intraocular lenses of the present disclosure increase depth of focus for improved near vision while maintaining the desired improvement in distance vision.

While anterior optical surface 122 of the intraocular lens 120 has been described as having three regions with varying asphericity profiles, in other embodiments the anterior optical surface includes fewer regions (i.e., two regions) or more regions (e.g., four, five, six, seven, eight, or more regions). Generally, regardless of the number of regions, each of the regions has an asphericity profile that is different from at least the asphericity profiles of the adjacent regions. Further, while the regions 126, 128, and 130 of the anterior optical surface 122 have been described as being separate and distinct regions with entirely separate asphericity profiles, it is understood that in some embodiments there is a transition area joining adjacent regions to facilitate a smooth transition between the different asphericity profiles. In that regard, in some instances the transition area has an asphericity profile that is defined by a combination of the asphericity profiles of the adjacent regions.

Generally, the intraocular lenses of the present disclosure may be formed of any suitable biocompatible lens material. For example, in some instances the lenses are formed of a soft acrylic polymer (e.g., a material used to form commercially available lenses sold by Alcon under the trademark Acrysof®). The intraocular lenses of the present disclosure may be formed of the materials disclosed in U.S. Pat. No. 6,416,550, which is hereby incorporated by reference in its entirety. In some instances, the intraocular lenses are foldable to facilitate insertion using minimally invasive surgical techniques. In particular, the intraocular lenses may be configured to be inserted through an incision having a length less than 4.0 mm and, in some instances, less than 3.5 mm. Further, it is understood that in some embodiments the intraocular lenses will include haptics (not shown) to facilitate proper positioning of the intraocular lens within the eye. In some embodiments, the intraocular lenses are configured to interface with an intraocular ring.

Although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:
1. An intraocular lens, comprising:
a body portion defining an anterior optical surface and an opposing posterior optical surface, the anterior optical surface including:
a central region extending radially outward from a center point of the body portion a first distance, the central region having a first asphericity profile,
a first outer region extending radially outward from the central region, the first outer region having a second asphericity profile that is different than the first asphericity profile, and
a second outer region extending radially outward from the first outer region, the second outer region having a third asphericity profile that is different than the second asphericity profile, wherein each of the central region, the first outer region, and the second outer region have the same base refractive power, wherein the first outer region comprises an annular ring surrounding the central region such that the first outer region has a circular inner boundary defined by the first distance and a circular outer boundary defined by a second distance from the center point, wherein the second outer region comprises an annular ring surrounding the first outer region such that the second outer region has a circular inner boundary defined by the second distance and a circular outer boundary defined by a third distance from the center point, and wherein each of the first asphericity profile, the second asphericity profile, and the third asphericity profile are defined by the following equation:

$$Sag = \frac{cr^2}{1+\sqrt{1-(1+k)c^2r^2}} + \alpha_2 r^4 + \alpha_3 r^6,$$

where c, k, $\alpha_2$, and $\alpha_3$ are constants and r is a radius from the center point;

wherein each of the first asphericity profile, the second asphericity profile, and the third asphericity profile is characterized by a unique combination of constants c, k, $\alpha_2$, and $\alpha_3$ and wherein at least one of $\alpha_2$ and $\alpha_3$ has a different value for each of the first, second, and third asphericity profiles.

2. The lens of claim 1, wherein each of the central region, the first outer region, and the second outer region have the same conic constant.

3. The lens of claim 2, further comprising a third outer region extending radially outward from the second outer region, the third outer region having a fourth asphericity profile that is different than the third asphericity profile.

4. The lens of claim 2, wherein the posterior surface has either a spherical profile or a toric profile.

5. The lens of claim 1, wherein the first distance is between about 0.25 mm and about 2.0 mm.

6. The lens of claim 5, wherein the second distance is between about 0.5 mm and about 2.5 mm.

7. The lens of claim 6, wherein the third distance is between about 2.5 mm and about 3.0 mm.

8. The lens of claim 7, wherein the circular outer boundary of the second outer region is an outer boundary of the body portion.

9. The lens of claim 1, wherein c has the same value for each of the first, second, and third asphericity profiles, wherein k has the same value for each of the first, second, and third asphericity profiles, wherein $\alpha 2$ has a different value for each of the first, second, and third asphericity profiles, and wherein $\alpha 3$ has a different value for each of the first, second, and third asphericity profiles.

10. The lens of claim 9, wherein 1/c=18.990, wherein k=−3.159, wherein $\alpha 2$=6.034E-05 for the first asphericity profile, wherein $\alpha 2$=1.930E-04 for the second asphericity profile, wherein $\alpha 2$=−4.680E-04 for the third asphericity profile, wherein $\alpha 3$=1.164E-05 for the first asphericity profile, wherein $\alpha 3$=−1.527E-04 for the second asphericity profile, and wherein $\alpha 3$=3.541E-06 for the third asphericity profile.

* * * * *